US007211445B2

(12) United States Patent
Pozsgay

(10) Patent No.: US 7,211,445 B2
(45) Date of Patent: May 1, 2007

(54) CONJUGATION OF BIOMOLECULES USING DIELS-ALDER CYCLOADDITION

(75) Inventor: Vince Pozsgay, Washington, DC (US)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 299 days.

(21) Appl. No.: 10/692,411

(22) Filed: Oct. 22, 2003

(65) Prior Publication Data
US 2004/0082067 A1 Apr. 29, 2004

Related U.S. Application Data

(62) Division of application No. 09/919,637, filed on Aug. 1, 2001, now Pat. No. 6,673,905.

(60) Provisional application No. 60/223,959, filed on Aug. 9, 2000.

(51) Int. Cl.
G01N 33/548 (2006.01)
G01N 33/552 (2006.01)
G01N 33/553 (2006.01)
G01N 33/545 (2006.01)
C07K 17/10 (2006.01)
A61K 39/385 (2006.01)

(52) U.S. Cl. ............... 436/529; 424/193.1; 424/194.1; 436/525; 436/527; 436/531; 436/530; 530/405

(58) Field of Classification Search ................ 530/405; 435/6; 436/529, 530, 525, 527, 531; 424/193.1, 424/194.1
See application file for complete search history.

(56) References Cited

U.S. PATENT DOCUMENTS 5,874,532 A  2/1999 Picken et al.
6,171,797 B1 *  1/2001 Perbost ........................ 435/6

FOREIGN PATENT DOCUMENTS

WO  98/30575  *  7/1998
WO  00/31102  *  6/2000

OTHER PUBLICATIONS

Bernstein et al., *Carbohydr. Res.* 78:C1-C3, 1980.
Davis, *J. Chem. Soc. Perkin 1* 3215-3237, 1999.
Davis et al., *Synlett* 1495-1507, 1999.
Gray, *Archives of Biochemistry and Biophysics* 163:426-428, 1974.
Hill et al., Book of Abstracts, 214th ACS National Meeting, Las Vegas, NV, Sep. 7-11, ORGN-231, 1997.
Hill et al., *J. Org. Chem.* 66:5352-5358, 2001.
Jennings et al., *Neoglycoconjugates, Preparation and Applications* (Lee et al., Eds.), Academic Press, 325-371, 1994.
Jennings et al., *Polysaccharides in Medicinal Applications* (Dumitriu, S., Ed.), Marcel Dekker, Inc., 443-479, 1996.
Kallin, *Methods Enzymol.* 242:119-123, 1994.
Lubineau et al., *J. Org. Chem.* 52:1001-1007, 1987.
Lubineau et al., *J. Org. Chem.* 3011-3015, 1990.
Pinto et al., *Carbohydr. Res.* 124:313-318, 1983.
Pozsgay, *J. Org. Chem.* 63:5983-5999, 1998.
Romanowska et al., *Methods Enzymol.* 242:90-101, 1994.
Yousaf et al., *J. Am. Chem. Soc.* 121:4286-4287, 1999.
Yousaf et al., *Angew. Chem. Int. Ed.* 40(6), 2001, 1093-1096.
Garner, "Diels-Alder reactions in aqueous media," *Organic Synthesis in Water* (Grieco, P.A., Ed.), Blackie Academic and Professional, pp. 1-46, 1998.

* cited by examiner

Primary Examiner—Mary E. Ceperley
(74) Attorney, Agent, or Firm—Klarquist Sparkman, LLP

(57) ABSTRACT

A method is provided for covalently linking carbohydrates, proteins, nucleic acids, and other biomolecules under neutral conditions, using a Diels-Alder cycloaddition reaction. In an example, activated carbon-carbon double bonds were attached to free amino sites of a carrier protein, and a conjugated diene was attached to a carbohydrate hapten. Spontaneous coupling of the carbohydrate and the protein components under very mild conditions provided glycoconjugates containing up to 37 carbohydrate hapten units per carrier protein molecule. The method is also applicable to the immobilization of biomolecules on gel or solid supports. The conjugated products are useful as immunogens and as analytical and diagnostic reagents.

13 Claims, 2 Drawing Sheets

CONJUGATION OF BIOMOLECULES USING DIELS-ALDER CYCLOADDITION

PRIORITY CLAIM

This application is a divisional of U.S. patent application Ser. No. 09/919,637, filed Aug. 1, 2001, now U.S. Pat. No. 6,673,905 which claims the benefit of U.S. Provisional Patent Application No. 60/223,959, filed Aug. 9, 2000. Both of the prior applications are incorporated by reference herein in their entirety.

FIELD OF THE INVENTION

The invention is in the filed of bioorganic chemistry, more specifically the field of conjugation of biomolecules. The conjugated products prepared by the methods of the invention are useful, for example, as inoculants for the generation of antibodies, and as vaccines. The methods of the invention may also be used to immobilize biomolecules on solid supports. The immobilized biomolecules are useful in many fields, such as for example catalysis, separation, analysis, and diagnostics.

BACKGROUND

The conjugation of biomolecules to solid and gel supports is a common operation in may laboratories, and many methods have been developed for this purpose. Immobilization of enzymes (I. Chernukhin, E. Klenova, *Anal. Biochem.* 2000, 280:178–81), oligonucleotides (J. Andreadis; L. Chrisey, *Nucleic Acids Res.* 2000, 28:e5; A. Drobyshev et al., *Nucl. Acids. Res.* 1999, 27:4100–4105), antibodies (P. Soltys, M. Etzel, *Biomaterials* 2000, 21:37–48), and antigens (M. Oshima, M. Atassi, *Immunol. Invest.* 1989, 18:841–851) on solid and gel supports enables the preparation of useful products such as chromatographic media (*Meth. Enzym.* W. Jakoby, M. Wilchek, eds., 1974, 34, Academic Press, NY), catalysts (T. Krogh et al., *Anal. Biochem.*, 1999, 274:153–62), biosensors (J. Spiker, K. Kang, *Biotechnol. Bioeng.* 1999, 66:158–63), and numerous diagnostic (G. Ramsay, *Nature Biotechnol.,* 1998, 16:40–44) and research tools (C. Bieri et al., *Nature Biotechnol.* 1999, 17:1105–1108). Even whole cells may be immobilized by such methods (E. Olivares, W. Malaisse, *Int. J. Mol. Med.* 2000, 5:289–290).

The most robust form of attachment of a biomolecule to a surface or other support is via covalent bonds. Typically, such bonds are heteroatom-based (e.g., amide, ester, and disulfide bonds), because such bonds are easily formed under mild conditions. Non-covalent attachment via specific binding pairs (e.g., biotin-avidin or antibody-antigen interactions) is also commonly employed, but such methods still require initial conjugation of the specific binding pairs to the biomolecule and support. The use of carbon-carbon bonds for this purpose is very rare, because formation of C—C bonds is more difficult, especially under the mild aqueous conditions appropriate for working with proteins.

The use of the Diels-Alder reaction to attach a member of a specific binding pair has been described. In this report (M. N. Yousaf and M. Mrksich, *J. Am. Chem. Soc.,* 1999, 121:4286), a Diels-Alder reaction was used to covalently attach a biotinylated diene to an immobilized dienophile, and the immobilized biotin was subsequently used to non-covalently immobilize streptavidin. Thee workers have more recently used a Diels-Alder reaction to immobilize the peptide RGDS on a self-assembled alkanethiol monolayer on a gold surface (M. N. Yousaf, B. T. Houseman, M. Mrksich, *Angew. Chem. Int. Ed. Engl.,* 2001, 40:1093). The use of the Dials-Alder reaction to effect the actual covalent coupling or immobilization event of large biomolecules, however, had not previously been described.

The conjugation of biomolecules to one another is likewise a very common procedure, and is subject to most of the concerns and limitations described above for biomolecule immobilization. Covalent attachment of haptens to proteins has been a target of synthetic endavors since the discovery by Landsteiner that this process can convert non-immunogenic molecules to immunogenic material (K. Landsteiner, H. Lampl, *Biochem. Zeitschr.* 1918, 86:343). The application of this concept to carbohydrates by Goebel and Avery revealed that covalent carbohydrate-protein conjugates are immunogenic and can generate anti-carbohydrate antibodies (W. Goebel, *J. Exp. Med.* 1940, 72:33). The use of Landsteiner's principle has led to the development of carbohydrate-protein conjugates that are valuable tools in glycomedical research, and that are useful as pharmaceuticals. In particular, protein conjugates of fragments of the capsular polysaccharide of *Haemophilus influenzae* type b have become established as successful vaccines (J. Robbins et al., *J. Am. Med. Assoc.* 1996, 276:1181). Several other bacterial saccharide-protein conjugates are in various stages of clinical studies (E. Kondau et al., *J. Infect. Dis.* 1998, 177: 383–387; E. Konadu et al., *Infect. Immun.* 2000, 68:1529–1534) while numerous others are in the pre-clinical phase (V. Pozagay et al., *Proc. Natl. Acad. Sci. USA* 1999, 96:5194).

The choice of methods for covalent bond formation between biomolecules such as carbohydrates and proteins is restricted by their limited solubility in organic solvents, and in many cases by their pH and temperature sensitivity. In almost all cases, water is the only solvent that can be used for conjugation of carbohydrates or proteins, and the conditions are usually limited to temperatures under 50° C. and pH values between 6 and 8.

Numerous methods have been developed for the attachment of polysaccharides to proteins (C. Peeters et al., in *Vaccine Protocols*, A. Robinson et al., Eds., 1996 Humana Press, NJ, p. 111; W. Dick, Jr., M. Beurret, in *Contrib. Microbiol. Immunol.*, J. Cruse and R. Lewis, eds., 1989, 10:48–114, Karger, Basel; H. Jennings, R. Sood, in *Neoglycoconjugates. Preparation and Applications*. Y. Lee, R. Lee, eds., Academic Press, New York, 1994, p. 325). However, only a few of these methods are capable of coupling oligosaccharides to carriers in a site-selective fashion. Most prominent among these is reductive amination, which converts the reducing-end residue of the polysaccharide into a polyhydroxy alkylamino moiety, which unfortunately causes the loss of this unit as a true carbohydrate in the resulting glycoconjugate (V. Pozgay, *Glycoconjugate J.* 1993, 10:133).

This problem can be solved by chemical synthesis of oligosaccharide glycosides with aglycons that bear a (latent) reactive group. Examples include alkenyl groups (M. Nashed, *Carbohydr. Res.* 1983, 123:241–246; J. Allen, S. Danishefsky, *J. Am. Chem. Soc.* 1999, 121:10875), 3-aminopropyl (G. Veeneman et al., *Tetrahedron* 1989, 45:7433), 4-aminophenylethyl (R. Eby, *Carbohydr. Res.* 1979, 70:75), 4-aminophenyl (S. Stirm et al., *Justus Liebigs Ann. Chem.* 1966, 696:180), 6-aminohexyl (J. Hermans et al., *Rec. Trav. Chim. Pays-Bas* 1987, 106:498; R. Lee et al., *Biochemistry* 1989, 28:1856), 5-methoxycarbonylpentyl (S. Sabesan, J. Paulson, *J. Am. Chem. Soc.* 1986, 108:2068; V. Pozsgay, *Org. Chem.* 1998, 63:5983), 8-methoxycarbonyloctyl (R.

Lemieux et al., *J. Am. Chem. Soc.* 1975, 97, 4076; B. Pinto et al., *Carboydr. Res.* 1991, 210, 199) 4-aminobenzyl (W. Goebel, *J. Exp. Med.* 1940, 72:33), ω-aldehydoalkyl (V. Pozsgay, *Glycoconjugate J.* 1993, 10:133), 3-(2-aminoethylthio)propyl (Y. Lee, R. Lee, *Carbohydr. Res.* 1974, 37:193), 2-chloroethylthiogly (M. Ticha et al., *Glycoconjugate J.* 1996, 13:681) and 1-O-succinimide derivatives (M. Andersson, S. Oscarson, *Bioconjugate Chem.* 1993, 4:246; B. Davis, *J. Chem. Soc. Perkin I* 1999, 3215).

These aglycons introduce spacers that can be linked to a protein either directly or after insertion of a secondary linker. For this purpose the use of an activated dicarboxylic acid has been reported (R. van den Berg et al., *Eur. J. Org. Chem.* 1999, 2593–2600). In another procedure, a sulfhydryl group at the terminal position of the spacer allows the formation of a disulfide bridge with proteins using the dithiopyridyl method (J. Evenberg et al., *J. Infect. Dis.* 1992, 165(sup. 1):S152). In a related protocol, a thiolated protein is coupled with a maleimido-derivatized saccharide (J. Mahoney, R. Schnaar, *Methods Enzymol.* 1994, 242:17). N-acryloylamidophenyl glycosides may be coupled to unmodified proteins using a Michael addition (A. Romanowska et al., *Methods Enzymol.* 1994, 242:90). As an alternative to glycoside formation, direct coupling of a carbohydrate to a linker via amide bonds has also been used (A. Fattom et al., *Infect. Immun.* 1992, 60:584–589), but this approach is limited to carboxyl-containing carbohydrates.

The yields of any of these methods rarely exceed 40% and are generally in the 10–20% range (R. van den Berg et al., *Eur. J. Org. Chem.* 1999, 2593–2600), especially when medium or high carbohydrate loading in the conjugate is attempted. This problem is compounded by the fact that the oligosaccharide haptens, usually obtained in multistep syntheses or by controlled degradation of polysaccharides, can rarely be reconverted in their active or activable form after the coupling procedure. An additional problem with most chemical coupling methods employed to date is the formation of cross-linked byproducts, due to the presence of multiple reactive functional groups (e.g., amines, acids, hydroxyls, and sulfhydryls) on most biomolecules. Avoidance of this problem requires that the reactive groups be blocked, with requires additional processing steps and may alter the physicochemical and immunological properties of the biomolecule. Thus, there remains a need for a mild and site-selective method for coupling biomolecules to one another, which avoids the problems of low yields, crosslinking, and loss of starting materials. For similar reasons there remains a need for mild and selective methods for attaching biomolecules to surfaces and solid and gel supports.

BRIEF DESCRIPTION OF THE INVENTION

The present invention provides and experimentally simple protocol for the convalent attachment of biomolecules to one another and to supports, that can avoid many of the above-mentioned problems. The invention makes use of the well-known Diels-Alder cycloaddition reaction that takes place between a double bond and conjugated diene. This reaction has traditionally been carried out in organic solvents, but can proceed in aqueous solutions as well (R. Breslow, D. Rideout, *J. Am. Chem. Soc.* 1980, 102:7816; A. Lubineau, J. Auge, *Top. Curr. Chem.* 1999, 206:1; P. Garner, in *Organic Synthesis in Water*, P. Gricco, ed., Blackie Academic and Professional, London, 1998, p. 1.)

Carbohydrates have been employed as chiral auxiliaries and/or water solubilizing agents for Diels-Alder reactions, wherein a conjugated diene system is converted to a glycoside prior to the cycloaddition (A. Lubineau et al., *J. Chem. Soc. Perkin 1* 1997, 2863–2867; see also S. Pellegrinet, R. Spanevello, *Org. Lett.* 2000, 2:1073–1076). As noted above, the Diels-Alder reaction has also been used to covalently attach biotin to a support (M. N. Yousaf and M. Mrksich, *J. Am. Chem. Soc.,* 1999, 121:4286). However, the Diels-Alder reaction has not previously been extended to the direct covalent conjugation of biopolymers or other types of polymeric materials. Among the advantages of the method of the invention are the mild and neutral conditions, good yields, negligible cross-linking, and facile recovery of excess and/or unreacted biomolecules in their conjugatable form.

The invention also provides conjugated biomolecules, which are useful as immunostimulatory agents for production of antibodies and induction of immunity, methods of inducing antibody production with the conjugated biomolecules, and vaccine compositions comprising the conjugated biomolecules.

The invention also provides polyclonal and monoclonal antibodies generated by administration of the conjugated biomolecules to a mammal, and methods of using the induced antibodies for inducing passive immunity. The antibodies are useful of therapeutic, diagnostic, and analytical purposes.

The invention also provides immobilized biomolecules, and methods for their preparation, which are useful in many areas, such as chromatographic media, catalysts, components of diagnostic devices, biosensors, and as research tools.

DETAILED DESCRIPTION OF THE INVENTION

Figure 1:
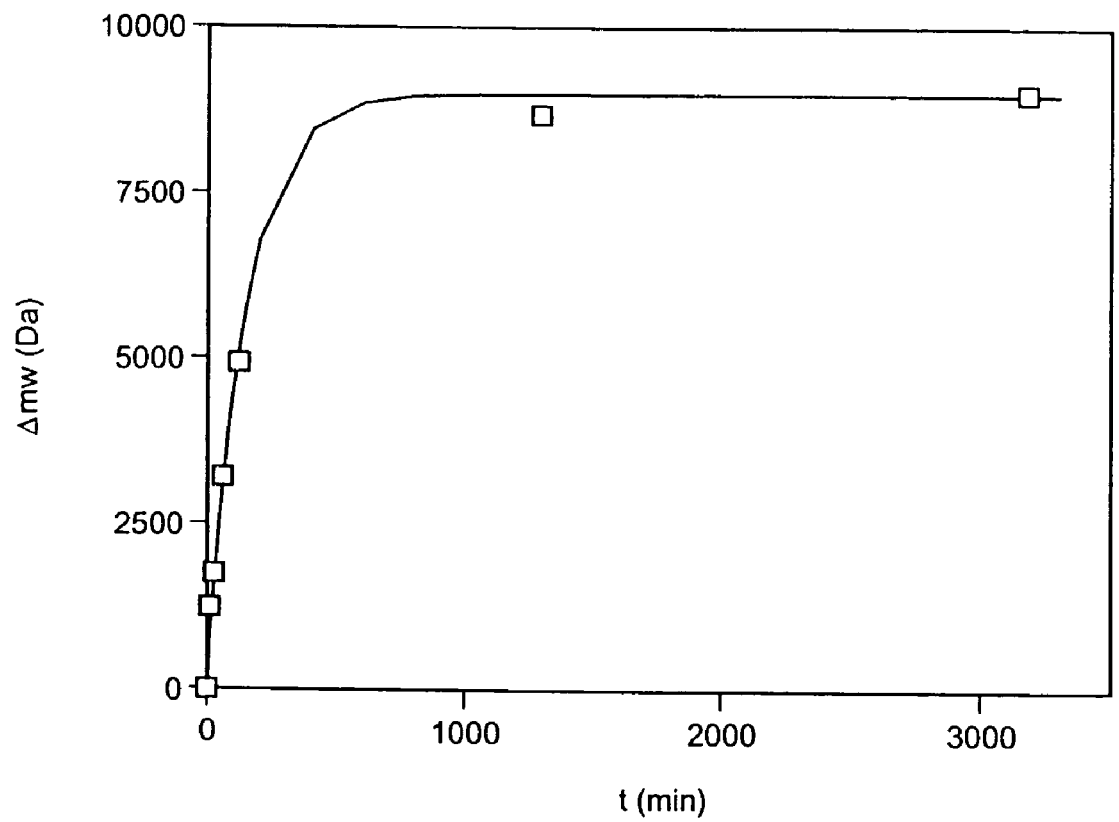
FIG. 1 illustrates the increase in molecular weight as a function of time of a conjugate (conjugate 28) of the invention relative to the mass of the core protein with the dienophiles attached.

The invention provides a new method for conjugation of biomolecules based on the Diels-Alder cycloaddition reaction. The technique involves the introduction of an activated double bond into a first biomolecule component, and a conjugated diene into a second biomolecule component, which are to be covalently linked together. The diene- and dienophile-modified biomolecules may then be purified to the extend desired. The two components are then simply combined under neutral conditions, and the cycloaddition reaction is allowed to proceed.

As used herein, the term "biomolecule" refers generally to the large, complex molecules produced within living cells, and to synthetic and simi-synthetic analogues thereof. Examples include proteins, peptides, oligo- and poly-saccharides, and oligo- and poly-nucleic acids, and various combinations thereof such as for example glycoproteins and nucleoproteins. Larger complexes, such as ribosomes, cellular substructures, and even entire cells are intended to fall within the meaning of the term as well.

In certain of the examples presented, the diene moiety is introduced into a carbohydrate component and the activated double bond into a polypeptide component. This may be reversed if desired, as a matter of convenience or if required by the synthetic design, as shown in another of the examples.

The cycloaddition step proceeds in most cases under neutral conditions, at or below physiological temperatures. Where they are of sufficiently low molecular weight, unreacted components can be recovered for re-use by simple diafiltration of the coupling reaction mixture.

The embodiment of the invention disclosed in certain of the examples below incorporates an electron-deficient carbon-carbon double bound into a protein, with human serum albumin (HSA) being used as an example and the commercially available reagent 3-sulfosuccinimidyl 4-maleimidobutyrate being used as the reagent. In these embodiments, the diene component of the Diels-Alder reaction is incorporated into a carbohydrate, with derivatives of trans,trans-hexa-2,4-dien-1-ol, 1-amino-hexa-2,4-diene, and octa-2,4-dienoic acid hydrazide being used as dienes. It will be understood that in general, the Diels-Alder reaction will occur between sterically accessible dienes and dienophiles regardless of the nature of the attached biomolecules, and that by appropriate selection of reagents both homoconjugates and heteroconjugates of proteins, carbohydrates, and oligonucleotides can be carried out by the methods of this invention.

The methods of the invention unexpectedly provide for a degree of control over the rate of coupling of the diene and dienophile components, simply by modification of the linker moieties. The molecular weight of the conjugate approaches a limiting value as the coupling reaction proceeds, which depends on the mass of the carbohydrate being attached. The observed increase in molecular weight as a function of time may therefore be fit to a pseudo-first order reaction kinetic equation of the form $$\Delta mw = \Delta mw_{max}(1-e^{-kt})$$

where $\Delta mw$ is the increase in molecular weight, $\Delta mw_{max}$ is the maximum increase that could be obtained if all the protein-linked starting material were to react, k is the rate constant, and t is time. The curves drawn through the data of FIGS. 1 and 2 (see Example 5 for the experimental details) were obtained by fitting the parameters of this equation to the data. The results of this fitting are summarized in Table 2.

The faster incorporation of construct 27 relative to 8 is an interesting observation. The observed difference apparently correlates with the distance between the hydrophilic rhamnose moiety and the hydrophobic diene part of the molecule. According to Breslow, the accelerating effect of wear on the rate of Diels-Alder reactions is due to hydrophobic pacing of the reactants (R. Breslow, D. Rideout, *J. Am. Chem. Soc.* 1980, 102:7816). Such an effect should be more pronounced in compound 27, where the diene sector is more isolated from the hydrophilic portion, than in compound 8.

The Diels-Alder reaction requires a highly organized transition state, and the ability of the components of the present invention to achieve the proper geometry for cycloaddition despite the mass and bulk of the attached biomolecules is remarkable.

In a preferred embodiment of the invention, one of the biomolecules to be linked is a hapten or antigen, and the other is a carrier. In a particularly preferred embodiment, the hapten or antigen is a polysaccharide moiety. Examples of antigenic polysaccharides are the capsular polysaccharides of *Haemophilus influenzae* type b, *Neisseria meningitidis*, Group B Streptococci, *Salmonella typhi*, *E. coli*, and Pneumococci.

Carriers are chosen to increase the immunogenicity of the hapten or antigen, and/or to raise antibodies against the carrier itself which may be medically beneficial. Carriers that fulfill these criteria are known in the art (see, e.g., A. Fattom et al., *Infect. Immun.* 1990, 58, 2309–2312; Devi, J. Robbins, R. Schneerson, *Proc. Natl. Acad. Sci. USA* 1991, 88:7175–7179; S. Szu, X el al., *Infect. Immun.*, 1991, 59:4555–4561; S. Szu et al., *J. Exp. Med.*, 1987, 166: 1510–1524). A carrier can be a natural, semi-synthetic, or synthetic material containing one or more functional groups, for example primary and/or secondary amino groups, azido groups, hydroxyl groups, or carboxyl groups, to which a diene or dieneophile Diels-Alder reactant moiety can be attached. The carrier can be water soluble or insoluble, and is preferably a polypeptide.

Examples of water soluble polypeptide carriers include, but are not limited to, natural, synthetic, or semisynthetic peptides or proteins from bacteria or viruses, e.g., bacterial, bacterial outer membrane proteins, bacterial toxins and toxoids such as tetanus toxin/toxoid, diphtheia toxin/toxoid, *Pseudomonas aeruginosa* exotoxin/toxoid/protein, pertussis toxin/toxoid, and *Clostridium perfringens* exotoxins/toxoid. Viral proteins such as hepatitis B surface antigen and core antigen may also be used as carriers, as well as proteins from higher organisms such as keyhole limpet hemoxyanin, horseshoe crab hemocyanin, edestin, mammalian serum albumins, mammalian ganmma-globulins, and IgG.

Polysaccharide carriers include, but are not limited to, dextran, capsular polysaccharides from microorganisms such as the Vi capsular polysaccharide from *S. typhi*, which is described in U.S. Pat. No. 5,204,098, (incorporated by reference herein); Pneumococcus group 12 (12F and 12A) polysaccharides; *Haemophilus influenzae* type d polysaccharide; and certain plant, fruit, or synthetic oligo- or polysaccharides which are immunologically similar to capsular polysaccharides, such as pectin, D-glacturonan, oligogalacturonate, or polygalacturonate, for example as described in U.S. Pat. No. 5,738,855 (incorporated by reference herein).

Examples of water insoluble carriers include, but are not limited to, aminoalkyl agarose, e.g., aminopropyl or aminohexyl SEPHAROSE (Pharmacia Inc., Piscataway, N.J.), aminopropyl glass, cross-linked dextran, and the like, to which a diene or dienophile can be attached. Other carriers may be used provided that a functional group is available for covalently attaching a diene or dienophile.

Examples of dienophiles include, but are not limited to, maleimides, acrylamides, azodicarboxylates, quinones, and 1,2,4-triazoline-3,5-diones. Examples of dienes include, but are not limited to, esters and glycosides of hexa-2,4-dien-1-ol, penta-2,4-dien-1-ol, furan-2-methanol, and furan-1-methanol; esters, amides, and hydrazides of octa-2,4-dienoic acid; and amides of 1-aminohexa-2,4-diene and 1- and 2-aminomethylfuran. The above-mentioned amines may also be coupled with aldehydo-biomolecules via reductive amination, and hydrazides may be attached to such biomolecules via condensation.

The invention also provides biomolecule conjugates of general formulas I and II below:

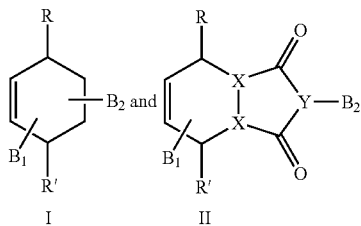

where R and R' are independently H or methyl, or together constitute $CH_2$, $CH_2CH_2$, $SO_2$, or O; X is CH or N; Y is N, CH=C, or NH—N; and $B_1$ and $B_2$ comprise biomolecules independently selected from the group consisting of polypeptides, carbohydrates, polysaccharides, and nucleic acids, and are optionally attached via a linker.

The invention also provides immobilized biomolecules of formulas I and II above, wherein one of $B_1$ and $B_2$ may be a solid or gel support. Examples of solid supports include, but are not limited to, aminopropylsilylated glass and silica surfaces, gold surfaces functionalized with thiol-bound linkers, functionalized macroporous polystyrene beads, and surface-derivatized microtiter plate wells. Examples of gel supports include, but are not limited to, functionalized agarose gels such as cyanogen bromide activated agarose, aminoethyl agarose, and carboxymethyl agarose.

The formulas above are intended to indicate that the group $B_1$ may be attached alpha or beta to the group R' as shown below:

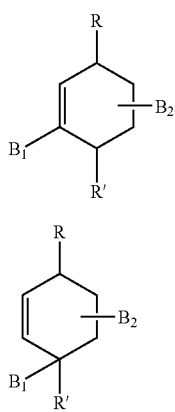

There are many known methods of attachment of small molecules to biomolecules, there are many known linker moieties for attachment of chemical moieties to biomolecules, and there are many known dienes and dienophiles that readily take part in cycloaddition reaction at or near room temperature. Those skilled in the art will thus appreciate that there are many obvious combinations of attachment methods, linkers, and diene and dienophile partners that may be employed in the method of biomolecule coupling disclosed herein, which are equivalent to the examples provided. Such modifications of the disclosed methods and resulting compositions are intended to be within the scope and spirit of the present invention.

It is another object of the invention to provide methods of using the polysaccharide-carrier conjugates of this invention for eliciting an immunogenic response in mammals, including but not limited to responses which provide protection against, or reduce the severity of, bacterial and viral infections. The pharmaceutical compositions of this invention are expected to be capable, upon injection into a mammal, of inducing serum antibodies against the polysaccharide component of the conjugate.

The invention also provides methods of using such conjugates, and/or pharmaceutical compositions comprising such conjugates, to induce in mammals, in particular, humans, the production of antibodies which immunoreact with the polysaccharide component of the conjugates. Antibodies which immunoreact with a bacterial or viral polysaccharide are useful for the identification or detection of microorganisms expressing the polysaccharide, and/or for diagnosis of infection. Antibodies against the polysaccharide may be useful in increasing resistance to, preventing, ameliorating, and/or treating illnesses caused by microorganisms or viruses that express the polysaccharide.

The compositions of this invention are intended for active immunization for prevention of infection, and for preparation of immune antibodies. The compositions of this invention are designed to induce antibodies specific to microorganisms expressing the polysaccharide component of the conjugate, and to confer specific immunity against infection with such microorganisms.

This invention also provides compositions, including but not limited to, mammalian serum, plasma, and immunoglobulin fractions, which contain antibodies which are immunoreactive with the polysaccharide component of the conjugates of this invention, and which preferably also contain antibodies which are immunoreactive with the protein component. These antibodies and antibody compositions may be useful to prevent, treat, or ameliorate infection and disease caused by the microorganism. The invention also provides such antibodies in isolated form. The invention further provides methods of inducing in mammals antibodies with immunoreact with a polysaccharide, the methods comprising administering to a mammal a composition of the invention.

The invention also provides monoclonal antibodies, preferably produced by hybridomas, which immunoreact with a polysaccharide. The nucleic acid sequences encoding these antibodies are obtained from a mammal in which the production of anti-polysaccharide antibodies has been induced by administering a composition of the invention.

As used herein, the terms "immunoreact" and "immunoreactivity" refer to specific binding between an antigen or antigenic determinant-containing molecule and a molecule having an antibody combining site, such as a whole antibody molecule or a portion thereof.

As used herein, the term "antibody" refers to immunoglobulin molecules and immunologically active portions of immunoglobulin molecules. Exemplary antibody molecules are intact immunoglobulin molecules, substantially intact immunoglobulin molecules and portion of an immunoglobulin molecule, including those portions known in the art as Fab, Fab', F(ab')hd 2 and F(v), as well as chimeric antibody molecules.

Polymeric Carriers

Carriers are chosen to increase the immunogenicity of the polysaccharide and/or to raise antibodies against the carrier which are medically beneficial. Carriers that fulfill these criteria are well-known in the art. A polymeric carrier can be a natural or a synthetic material containing one or more functional groups, for example primary and/or secondary amino groups, azido groups, or carboxyl groups, to which a diene or dienophile component can be attached. Carriers can be water soluble or insoluble. The examples below employ proteins as carriers.

Regardless of the precise method used to prepare the conjugate, after the Diels-Alder coupling reaction has been carried out the unreacted materials are preferably removed by routine physicochemical methods, such as for example dialysis, gel filtration or ion exchange column chromatography, depending on the materials to b separated. The final conjugate consists of the polysaccharide and the carrier bound through a Diels-Alder adduct.

Dosage for Vaccination

The present inoculum contains an effective, immunogenic amount of a polysaccharide-carrier conjugate. The effective amount of polysaccharide-carrier conjugate per unit dose sufficient to induce an immune response depends, among other things, on the immunogenicity of the polysaccharide, the species of mammal inoculated, the body weight of the mammal, and the chosen inoculation regimen, as is well known in the art. Inocula typically contain polysaccharide-carrier conjugates with concentrations of polysaccharide from about 1 micrograms to about 500 micrograms per inoculation (dose), preferably about 3 micrograms to about 50 micrograms per dose, and most preferably about 5 micrograms to 25 micrograms per dose.

The term "unit dose" as it pertains to the inocula refers to physically discrete units suitable as unitary dosages for mammals, each unit containing a predetermined quantity of active material (polysaccharide) calculated to produce the desired immunogenic effect in association with the required diluent.

Inocula are typically prepared in physiologically and/or pharmaceutically tolerable (acceptable) carriers, and are preferably prepared as solutions in physiologically and/or pharmaceutically acceptable diluents such as water, saline, phosphate-buffered saline, or the like, to form an aqueous pharmaceutical composition. Adjuvants, such as aluminum hydroxide, QS-21, TiterMax™ (CytRx Corp., Norcross Ga.), Freund's complete adjuvant, Freund's incomplete adjuvant, interleukin-2, thymosin, and the like, may also be included in the compositions.

The route of inoculation may be by intramuscular or subcutaneous injection or the like, so long as it results in eliciting antibodies reactive against the polysaccharide component. It is anticipated that in some cases the composition can be administered orally or intranasally, for example when mucosal immunity is to be induced. In order to increase the antibody level, a second or booster dose may be administered approximately 4 to 6 weeks after the initial administration. Subsequent doses may be administered as deemed necessary by the practitioner.

Antibodies

An antibody of the present invention is typically produced by immunizing a mammal with an immunogen or vaccine containing a polysaccharide-carrier conjugate, preferably a polysaccharide-protein conjugate, to induce in the mammal antibody molecules having immunospecificity for the polysaccharide component of the conjugate. Antibody molecules having immunospecificity for the protein carrier may also be produced. The antibody molecules may be collected from the mammal and, optionally, isolated and purified by methods known in the art.

Human or humanized monoclonal antibodies are preferred, including but not limited to those identified by phage display technology, and including but not limited to those made by hybridomas and by mice with human immune systems or human immunoglobulin genes. The antibody molecules of the present invention may be polyclonal or monoclonal. Monoclonal antibodies may be produced by methods well-known in the art. Portions of immunoglobulin molecules, such as Fabs, may also be produced by methods know in the art.

An antibody of the present invention may be contained in blood plasma, serum, hybridoma supernatants and the like. Alternatively, the antibodies of the present invention are isolated to the extend desired by well known techniques such as, for example, ion chromatography or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibodies of the IgG class are preferred for conferring passive immunity. The antibodies of the present invention have a number of diagnostic and therapeutic uses. The antibodies can be used as an in vitro diagnostic agents to test for the presence of microorganisms in biological samples or in water or food samples, in standard immunoassay protocols. Such assays include, but are not limited to, agglutination assays, radioimmunoassays, enzyme-linked immunosorbent assays, fluorescence assays, Western blots and the like. In one such assay, for example, the sample is contacted with first antibodies of the present invention, and a labeled second antibody is used to detect the presence of polysaccharides to which the first antibodies have bound.

Such assays may be, for example, of direct format (where the labeled first antibody is reactive with the polysaccharide), an indirect format (where a labeled second antibody is reactive with the first antibody), a competitive format (such as the addition of a labeled polysaccharide), or a sandwich format (where both labeled and unlabeled antibody are utilized), as well as other formats describe in the art.

In providing the antibodies of the present invention to a recipient mammal, the dosage of administered antibodies will vary depending upon such factors as the mammal's age, weight, height, sex, general and specific medical conditions, and the like.

In general, it is desirable to provide the recipient with a dosage of antibodies which is in the range of from about 1 mg/kg to about 10 mg/kg body weight of the mammal, although a lower or higher dose may be administered. The antibodies of the present invention are intended to be provided to the recipient subject in an amount sufficient to prevent, or lessen or attenuate the severity, extend or duration of the infection.

In order to facilitate the administration of the conjugates of the invention to mammals, it is preferred that the conjugate be formulated with a pharmaceutically acceptable carrier. (Those skilled in the art will appreciate the term "carrier," when used in this context, has a different meaning that when it is used to refer to a biomolecule component of the conjugate.) Examples of pharmaceutically acceptable carriers include sterile water and saline, both of which may be buffered with phosphate, citrate, and the like. The conjugates of the invention may be provided in solution or suspension in a pharmaceutically acceptable carrier, or they may be provided in dry form and reconstituted with the pharmaceutically acceptable carrier prior to administration.

The administration of the conjugates and compositions of the invention may be for prophylactic or therapeutic purposes. When provided prophylactically, the agents are provided in advance of any symptom. The prophylactic administration of the agent serves to prevent or ameliorate any subsequent infection. When provided therapeutically, the agent is provided at (or shortly after) the onset of a symptom of infection.

For all therapeutic, prophylactic and diagnostic uses, the polysaccharide-carrier conjugates of this invention, as well as antibodies and other necessary reagents and appropriate devices an accessories may be provided in kit form so as to be readily available and easily used.

The examples below will be understood to be merely representative of the invention, and are not intended to limit the scope of the appended claims in any way.

EXAMPLE 1

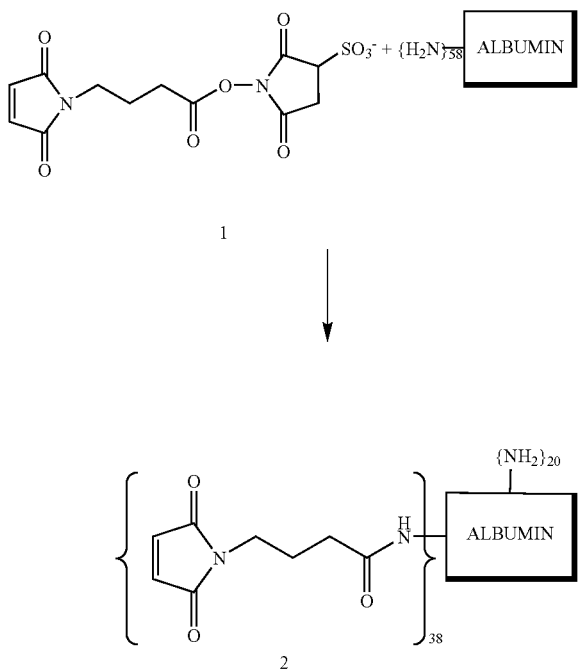

Dieneophile component 2: Treatment of human serum albumin (HSA) with a 1.6 molar excess (based on 58 available amino groups) of 3-sulfosuccinimidyl 4-maleimidobutyrate (1) in a pH 7.5 phosphate buffer afforded the intermediate 2, which contained an average of 38 maleimido moieties per protein molecule, as indicated in the formula (determined by MALDI-TOF mass spectroscopy).

Diene component 8: The phenylthio rhamnoside 3 was prepared as described previously (V. Pozsgay, *Carbohydr. Res.* 1992, 235:295). Rhamnoside 3 was treated with acetic anhydride and pyridine to afford 4, $^1$H NMR (CDCl$_3$, δ) 8.11–7.26 (m, 15 H), 5.79 (dd, 1 H), 5.64–5.52 (m, 3 H) 5.53 (t, 1 H, J=10.0 Hz), 4.49 (dq, 1 H), 1.89 (s, 2 J=6.3 Hz), $^{13}$C (CDCl$_3$, δ) 170.1, 165.7, 165.5, 133.5–127.9, 85.8, 72.1, 71.9, 69.5, 68.1, 20.6, 17.6.

From 4 the hemiacetal 5 was obtained by hydrolysis with mercuric tribluoroacetate (L. Yan, D. Kahne, *J. Am. Chem. Soc.* 1996, 118:9239), $^1$H NMR (CDCl$_3$, δ) 8.1–7.4 (m, 10H), 5.71 (dd, 1 H, J=3.4 Hz, J=9.9 Hz), 5.78 (dd, 1 H), 5.49 (t, 1 H, J=9.9 Hz), 5.38 (br d, 1 H), $^{13}$C (CDCl$_3$, δ) 170.3, 165.8, 92.2, 71.9, 71.0, 68.9, 66.7, 20.7, 17.7.

Hemiacetal 5 was converted to the trichloroacetimidate 6, and glycosylation of trasn,trans-hexa-2,4-dien-1-ol with 6 using CF$_3$SO$_3$Si(CH$_3$)$_3$ as the activator afforded the glycoside 7. The acetyl groups were then removed by treatment with NaOMe to afford the diene rhamnoside 8. $^1$H NMR (D$_2$O, δ) 6.33 (dd, 1 H, J=9.5 Hz, J=10.2 Hz), 6.16 (ddd, 1 H, J=1.6 Hz, J=10.2 Hz, J=14.8 Hz), 5.85 (m, 1 H), 4.83 (d, 1 H, J=1.7 Hz), 4.21 (dd, 1 H, J=6.4 Hz, J=12.4 Hz), 4.07 (dd, 1 H, J=7.1 Hz, J=12.4 Hz), 3.91 (dd, 1 H, J=1.7 Hz, J=3.4 Hz), 3.69 (dq, 1 H), 3.73 (dd, 1 H, J=3.4 Hz, J=9.6 Hz), H, J=9.6 Hz), 1.75 (d, 3 H, J=6.8 Hz), 1.28 (d, 3 H, J=6.3 Hz), $^{13}$C (D$_2$O, δ) 136.7, 132.7, 131.1, 125.6, 99.8, 72.8, 71.1, 71.0, 70.9, 69.4, 68.6, 18.2, 17.4.

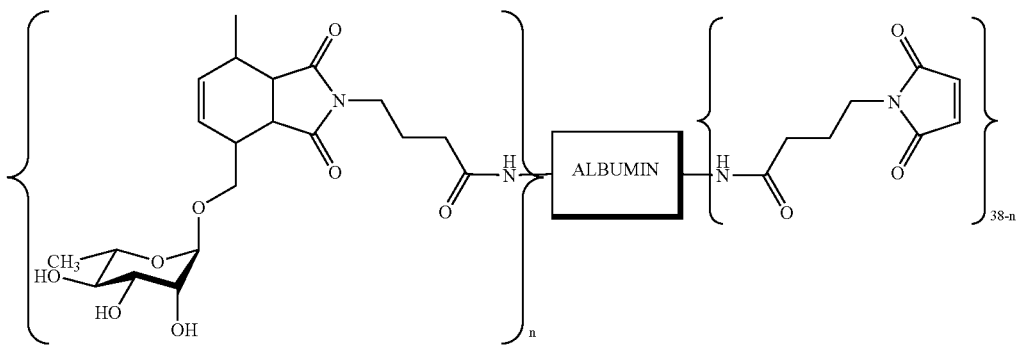

Coupling reaction: An excess of 8 was treated in an aqueous solution with the maleimido-derivatized protein 2. The average incorporations of the hapten, as a function of time and temperature, are shown in Table 1. This data was obtained from the average molecular mass of the conjugates determined by the MALDI-TOF method. As expected for a concerted cycloaddition reaction, the incorporation level depends on the reaction time and temperature. At room temperature, approximately 63% of the available dienophile moieties in the protein participated in adduct formation within 36 h, while at 40° C. almost complete utilization of these moieties occurred after four days (Table 1). The unreacted diene 8 was recovered by diafiltration, and the conjugate 9 (free amino groups not shown) was then obtained as a white solid after freeze-drying.

TABLE 1

Time and temperature dependence of the cycloaddition between 2 and 8

| Time (h) | Composition of the conjugate (mol hapten/mol albumin) | |
| --- | --- | --- |
| | 22° C. | 40° C. |
| 36 | 24 | 27 |// 
| 100 | 28 | 37 |

EXAMPLE 2

Dienophile component: The glycoside of 6-hydroxyhexanoic acid hydrazide with the tetramer of (α-L-rhamnopyranosyl)-(1→2)-(α-D-galactopyranosyl)-(1→3)-(α-D-glucopyranosyl)-(1→3)-α-L-rhamnopyranose is prepared, according to the procedure disclosed in international patent application WO 99/03871. Treatment with maleic anhydride provides an N-terminal maleimide derivative 10.

Diene component: Trans,trans-hexa-2,4-dien-1-ol and succinic anhydride are reacted in the presence of N,N-dimethylaminopyridine to provide trans,trans-hexa-2,4-dien-1-ol monosuccinate. An aqueous solution of an excess of the monosuccinate is activated with 1-[3-(dimethylamino)propyl]-3-ethylcarbodiimide and coupled with human serum albumin, to provide a poly(diene) derivative 11.

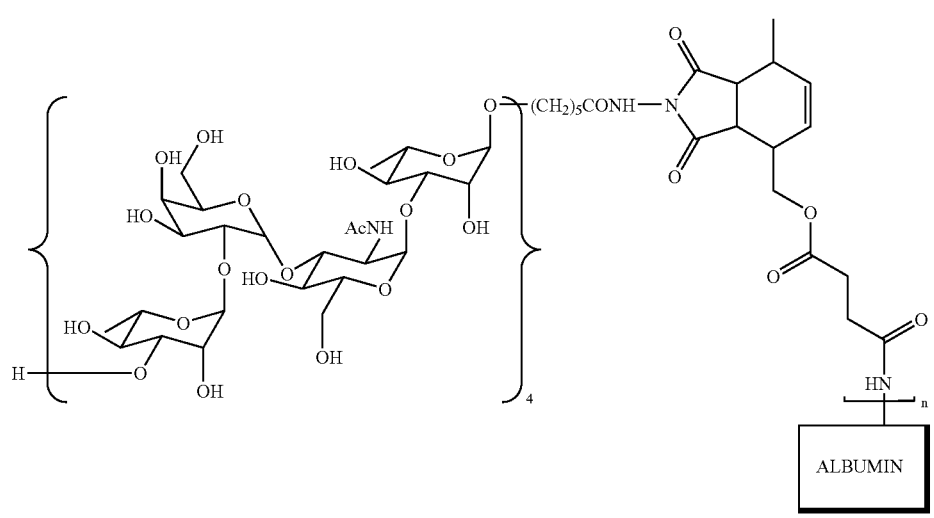

Coupling reaction: An aqueous solution of 11 and excess 10 is incubated at 35° C. for 4 days, and the resulting conjugate 12 (n≦58) is purified by diafiltration and lyophilized. The conjugate 12 is expected to be useful for inducing antibodies against *Shigella dysenteriae.*

EXAMPLE 3

Diene component: The Vi capsular polysaccharide of *Salmonella typhi* (Pasteur Merieux Serums et Vaccins, Lyon F R) is dissolved in water, excess 2,4-hexadienylamine is added, and the solution buffered to pH 5.0. A slight excess of 1-ethyl-3-[3-(dimethylamino)propyl]carbodiimide in water is added. After 4 h at 37°, the mixture is adjusted to pH 7.5 and dialyzed to remove excess reagents. The resulting solution of 13 is used immediately.

Dienophile component: Pseudomonas aeruginosa recombinant exoprotein A (Fattom el al., *Infect. Immun.* 1992, 60:584–589) is treated with excess 3-sulfosuccinimidyl 4-maleimidobutyrate (1) as in Example 1, followed by dialysis and lyophilization to provide a maleimide derivatized protein 14.

15

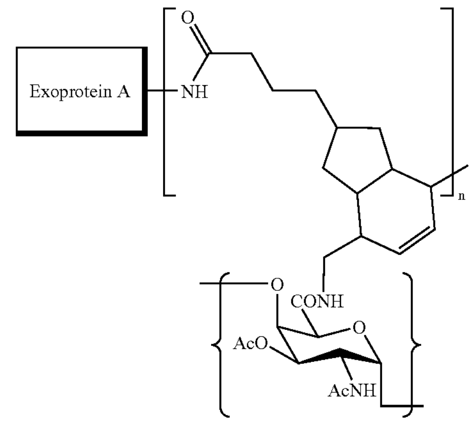

Coupling reaction: An excess of the diene 14 is added to the solution of dienophile component 13. After 4 days at 37° C., the mixture is concentrated, and conjugate 15 is purified by size exclusion chromatography on SEPHACRYL S-1000™ (Pharmacia, Piscataway N.J.). The conjugate 15 is expected to be useful for inducing antibodies against *Salmonella typhi.*

EXAMPLE 4

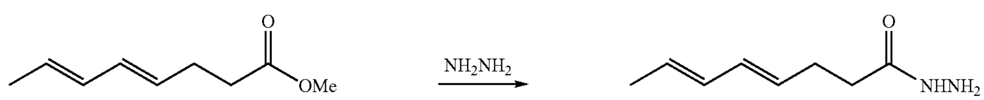

16 17

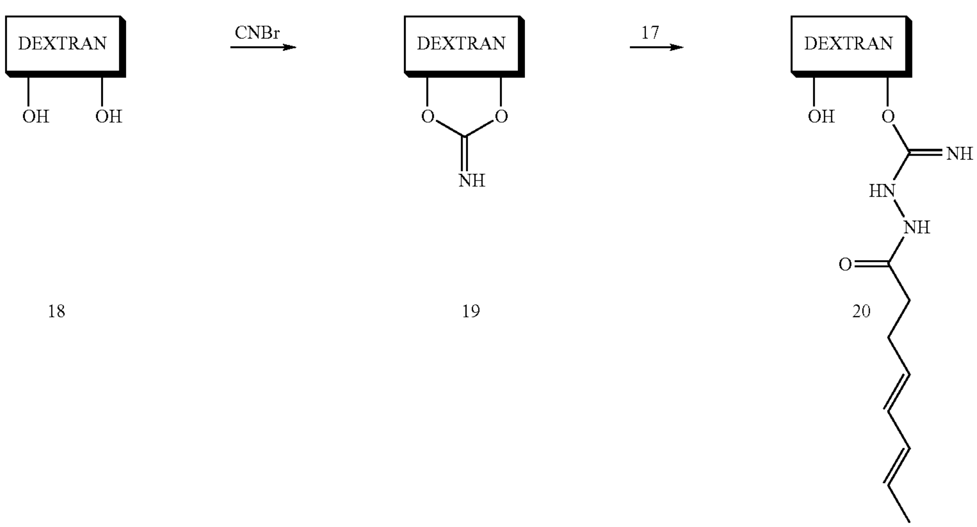

18 19 20

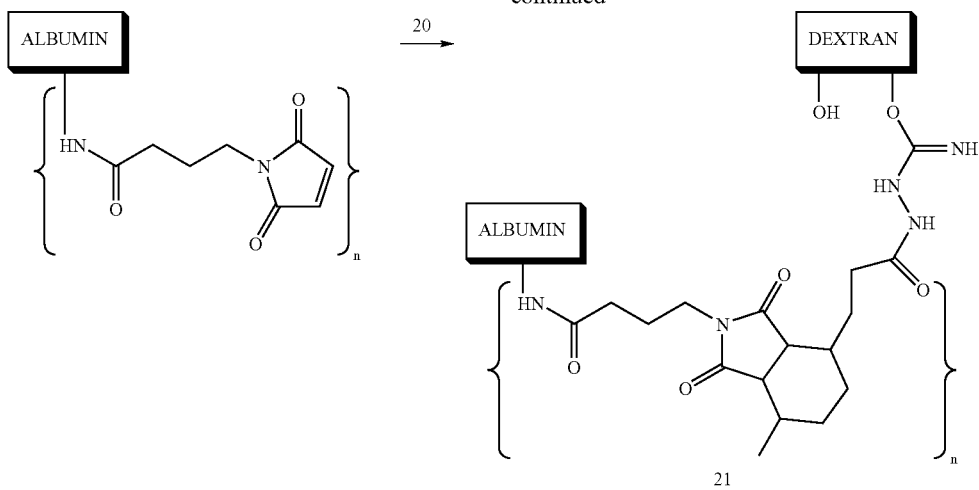

Diene component: To a solution of methyl octa-4,6-dienoate (16) (6 g) in methanol (10 ml) was added hydrazine (3 ml) at room temperature. After 24 h, the solution was diluted with water (50 ml). The crystalline precipitate was isolated by filtration to afford octa-4,6-dienoic acid hydrazide (17) as colorless microcrystals, yield 5.7 g. Dextran (nominal MW 10 kDa, Pharmacia) was diafiltered through a YM10 membrane (MW cutoff 10 kDa, Millipore) using 3 changes of water. The solution that passed through the membrane was diafiltered through a YM3 (MW cutoff 3000 Da) membrane, suing five changes of water. The material retained by the membrane was lyophilized. A stirred solution of the dextran 18 thus obtained (22.5 mg, 2.25 μmol, corresponding to 139 μmol of glucose) in $H_2O$ (2.2 ml) at 5° C. (ice bath) was equipped with a temperature-sensing pH electrode, and 0.1 M NaOH was added with a 100 μL microsyringe until the pH reached 10.5. To this solution was added BrCN (50 μL of a 5 M solution in acetonitrile). The pH of the solution was maintained between 10.5 and 10.8 by addition of 0.1 M NaOH with a microsyringe. After 6 min, the solution was adjusted to pH 8.5 by addition of pH 8.0 phosphate buffer (ca. 1 ml). To the reaction mixture was immediately added a solution of octa-4,6-dienoic acid hydrazide (3.5 mg, 235 μmol) in 0.5 ml dimethyl sulfoxide. The pH of the reaction mixture rose to 8.95, at a temperature of 9° C. The ice bath was removed and the stirred solution was allowed to reach 25° C. After 2.5 h, the pH was 8.18 and remained unchanged over 5 min. The solution of 20 was diafiltered through a YM-3 membrane using 5 changes of water (4 ml each).

Dienophile component: A stirred solution of human serum albumin (11.4 mg, 0.17 μmol, 9.88 μmol of amino groups) in pH 7.5 buffer (1 ml) was treated at 5° C. (ice-bath) with 3-sulfosuccinimidyl 4-maleimidobutyrate (1) (0.52 mg, 1.36 μmol). The solution was stirred for 15 min at 5° C. then for another 15 min at room temperature followed by diafiltration through a YM-10 membrane using 5 changes of water (4 ml each).

Coupling reaction: The residual solutions containing the modified dextran 20 and the modified human serum albumin were combined. The total volume of the combined solution was approx. 1 ml. After 22 h at room temperature, the reaction mixture was diafiltered through a YM-10 membrane using 6 changes of $H_2O$ (5 ml each), and the residue was freeze-dried. MALDI mass spectroscopy showed that most of the albumin is consumed. The conjugate 21 that is formed has average molecular weight of 90 kDa.

EXAMPLE 5

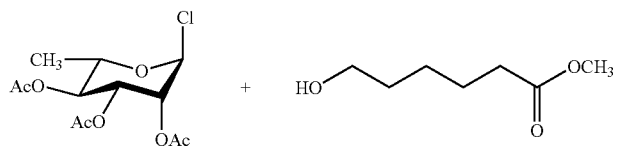

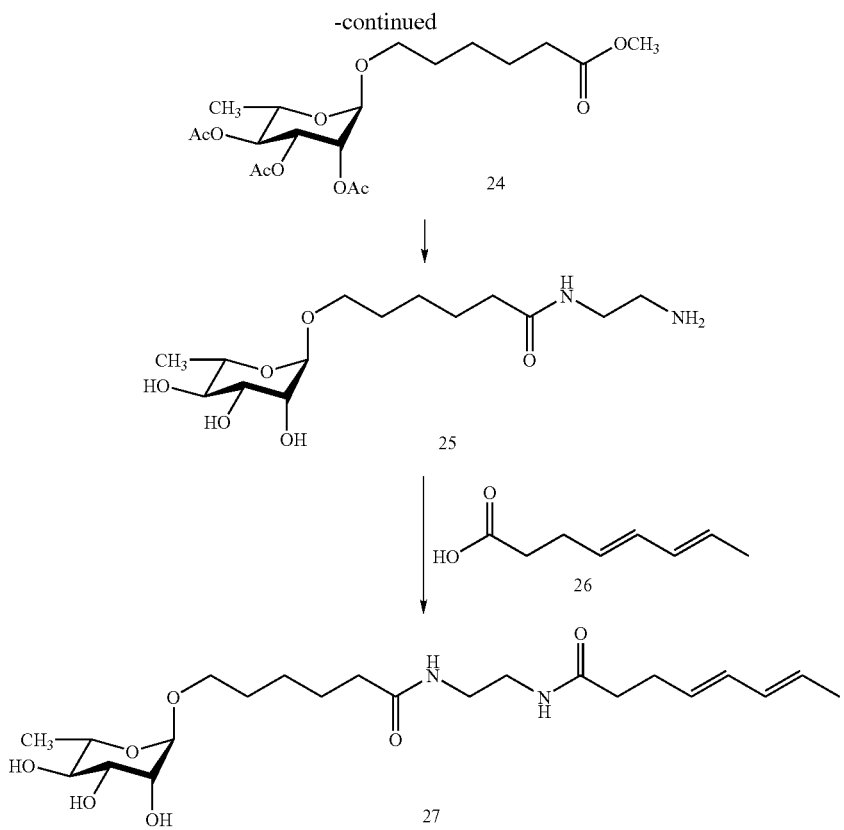

Diene component: 6-Hydroxyhexanoic acid 23 (S. Sabesan, J. C. Paulson, *J. Am. Chem. Soc.,* 1986, 108:2068) and glycosyl chloride 22 (V. Pozsgay, *Glycoconj. J.,* 1993, 10:133), in methylene chloride at −40° C., were treated with silver triflate and 2,6-di-t-butyl-4-methylpyridine for 10 min. to afford glycoside 24. Deprotection with a catalytic amount of NaOMe in MeOH at 23° C. for 24 hr, followed by treatment with ethylenediamine in ethanol at 80° C. for 12 hr, provided 25 in 74% overall yield. $^1$H NMR (500 MHz, $CD_3OD$): δ=4.64 (br s, 1 H), 3.78 (dd, 1 H), 3.66 (m, 1 H), 3.55 (dq, 1 H), 3.39 (m, 1 H), 3.35 (t, 2 H), 2.76 (t, 2 H), 2.21 (t, 2 H), 1.54–1.68 (m, 4 H), 1.35–1.46 (m, 2 H), 1.24 (d Octadienoic acid 26 was prepared from the corresponding methyl ester (T. Hudlicky et al., *J. Org. Chem.,* 1980, 45:5020). Acylation of 25 with 26 (dicyclohexyl-carbodiimide, EtOAc, MeOH) afforded the glycoside diene 27 in 92% yield, $^1$H NMR (500 MHz, $CD_3OD$): δ=6.09 (m, 2 H), 5.70 (m, 1 H), 5.57 (m,1 H), 4.77 (br s, 1 H), 3.92 (dd, 1 H), 3.63–3.75 (m, 4 H), 3.53 (m, 1 H), 3.43 (t, 1 H), 3.32 (m, 4 H), 2.32 (m, 4 H), 2.22 (m, 2 H), 1.72 (d, 3 H), 1.53–1.67 (m, 4 H), 1.30–1.42 (m, 2 H), 1.29 (d, 3 H), Dienophile component: A stirred solution of human serum albumin in pH 7.5 buffer (1 ml) was treated at 5° C. (ice-bath) with 3-sulfosuccinimidyl 4-maleimidobutyrate (1) as described above, to provide maleimido-derivatized protein containing an average of 29 maleimido groups per molecule of protein.

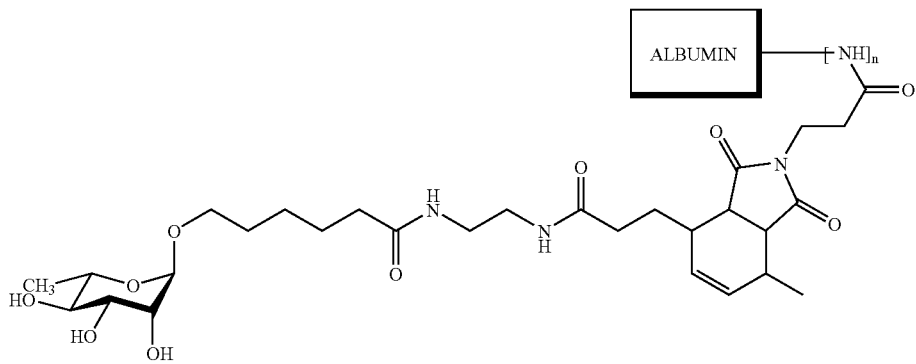

Coupling reaction: The diene 27 was treated with the maleimido-derivatized protein in water at 23° C. Samples taken at various times were diafiltered through a 10 kDa cutoff membrane then were lyophilized and subjected to MALDI-TOF mass spectrometry. The increase in molecular weight of the resulting conjugate 28 (n≦29), relative to the mass of the core protein with the dienophiles attached, is shown as a function of time in FIG. 1.

Figure 2:
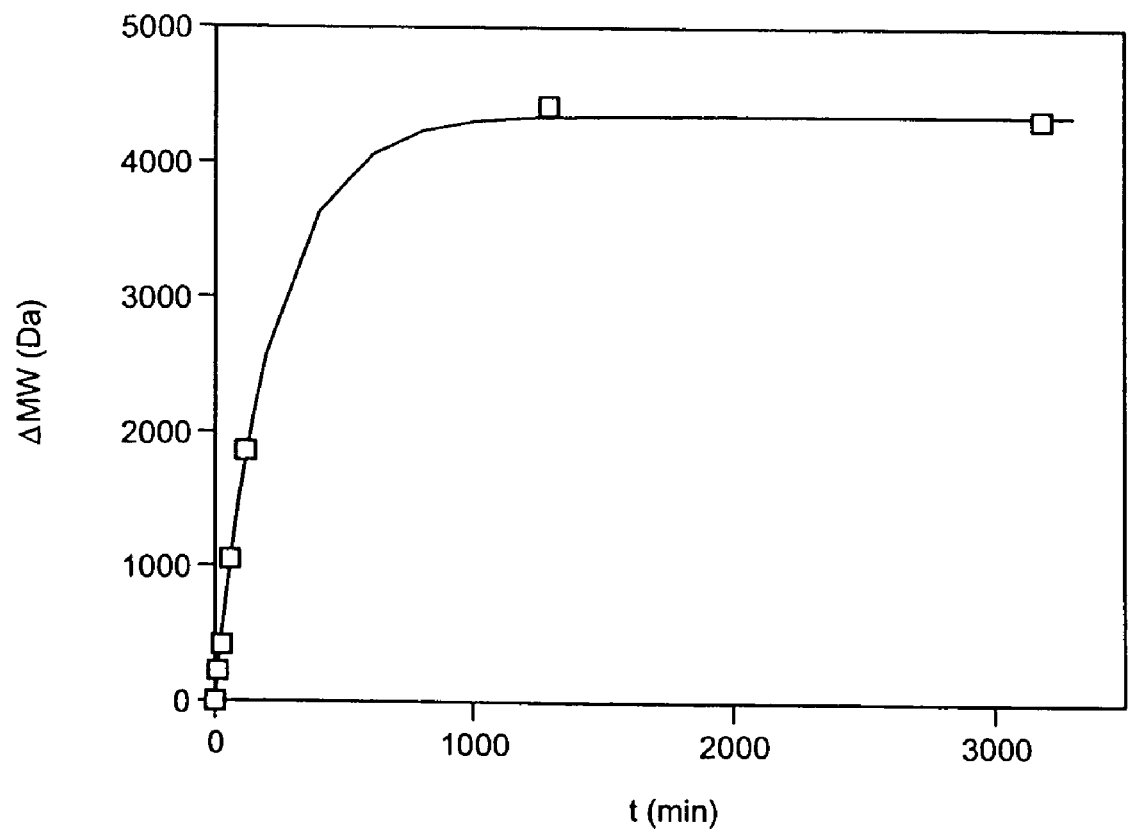
FIG. 2 illustrates a similar time-dependent experiment as represented in FIG. 1, conducted with the same maleimido-derivatized protein, using previously-described diene 8.

A similar time-dependent experiment was conducted with the same maleimido-derivatized protein, using previously described diene 8, and the results are shown in FIG. 2. Kinetic parameters are shown in Table 2.

TABLE 2

Kinetic Parameters for Conjugation Reactions

| | Parameters for $\Delta mw = \Delta mw_{max}(1 - e^{-kt})$ | | |
|---|---|---|---|
| Diene | $\Delta mw_{max}$ | k (min$^{-1}$) | $t_{1/2}$ (min) |
| 14 | 9000 | 0.007 | 99 |
| 8 | 4350 | 0.0045 | 154 |

EXAMPLE 6

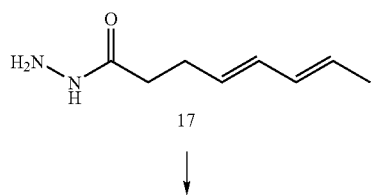

17

-continued

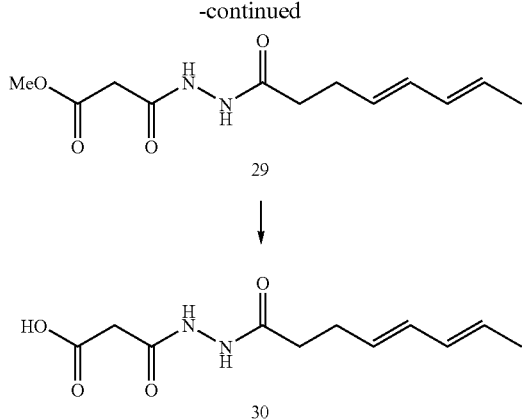

Diene component: The previously describe ester 16 was converted to hydrazide 17 by treatment with hydrazine in MeOH at 23° C. for 24 hr.: $^1$H NMR (500 MHz, CD$_3$OD): δ=6.00 (m, 2 H), 5.57 (m, 1 H), 5.49 (m, 1 H), 2.33 (m, 2 H), 2.21 ( (d, 3 H).

Acylation with methyl malonyl chloride in pyridine at −20° C. for 20 min afforded the ester 29 in 72% yield, $^1$H NMR (500 MHz, CD$_3$OD): δ=6.03 (m, 2 H), 5.58 (m, 2 H), 3.74 (s, 3 H), 3.41 (m, 2 H), 2.31–2.43 (m, 4 H), 1.23 (d, 3 H).

Hydrolysis with LiOH in methanol (23° C., 1 hr), followed by acidification with 1 N HCl, gave the crystalline acid 30 in 74% yield, $^1$H NMR (500 MHz, CD$_3$OD): δ=5.97 (m, 2 H), 5.52 (m, 2 H), 3.26 (m, 2 H), 3.24–3.37 (m, 4 H), 1.66 (d, 3 H).

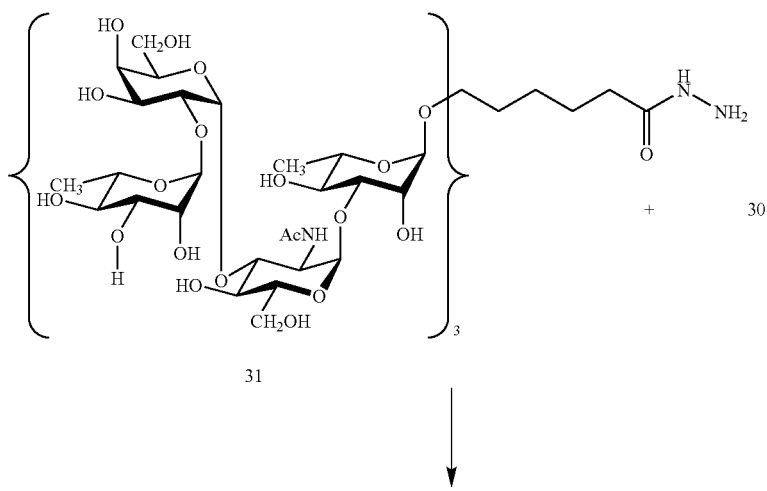

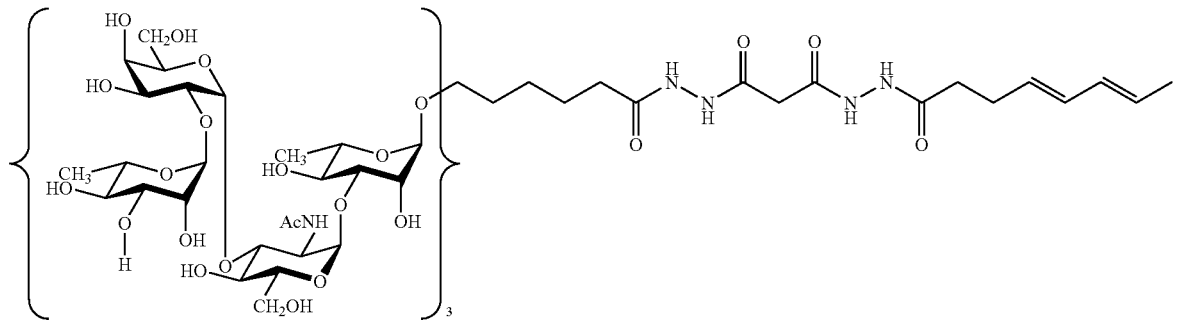

32

Treatment of the dodecasaccharide hydraxzide 31 (V. Pozsgay, *J. Org. Chem.* 1998, 63:5983) with the linker 30 in DMF in the presence of HATU led to the diene-equipped construct 32, which was purified by gel-filtration through a Biogel P-4 column using water as the eluant. $^1$H NMR (500 MHz, $D_2O$): δ=6.11 (m, 2 H), 5.72 (m, 1 H), 5.61 (m, 1 H), (br s, 3 H), 5.11 (br s, 2 H), 5.08 (br s, 1 H), 5.06 (br s, 2 H), 5.04 (d, 2 H), 5.00 (br s, 1 H), 1.71 (d, 3 H); FAB-MS (dithiothreitol-dithioerythritol, positive ion) 2363.9 (M+Na), calcd.: 2362.9.

Dienophile component: A stirred solution of human serum albumin in pH 7.5 buffer (1 ml) was treated at 5° C. (ice-bath) with 3-sulfosuccinimidyl 4-maleimidobutyrate (1) as described above, to provide maleimido-derivatized protein containing an average of 22 maleimido groups per molecule of protein.

Coupling reaction: Under conditions similar to those used for the conjugation of constructs 8 and 27, cycloaddition of 32 onto the maleimido-derivatized protein took place at a slower rate. After 2 hours, the average incorporation was 1.5 dodecasaccharide chains per HSA molecule, and after 8 hours, the incorporation reached an average of 3.

I claim:

1. A conjugate of biomolecules of the formula

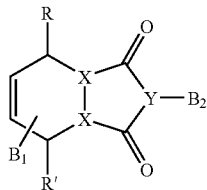

wherein R and R' are independently H or methyl, or together constitute $CH_2$, $CH_2CH_2$, or O; X is CH or N; Y is N, CH═C, or NH—N; and $B_1$ comprises a carbohydrate and $B_2$ comprises a peptide carrier, a protein carrier, or a polysaccharide carrier, or $B_1$ comprises a peptide carrier, a protein carrier, or a polysaccharide carrier and $B_2$ comprises a carbohydrate; and wherein $B_1$ is attached at a ring position that is the same ring position as R or R' and $B_1$ and $B_2$ are each individually optionally attached to the ring structure via a linker.

2. The conjugate of biomolecules according to claim 1, wherein one of the biomolecules is a polysaccharide.

3. The conjugate of biomolecules according to claim 2, wherein the polysaccharide is a viral or bacterial polysaccharide.

4. The conjugate of biomolecules according to claim 1, wherein one of the biomolecules is a polysaccharide and the other biomolecule is a polypeptide.

5. The conjugate of biomolecules according to claim 4, wherein the polysaccharide is a viral or bacterial polysaccharide.

6. An immobilized biomolecule of the formula

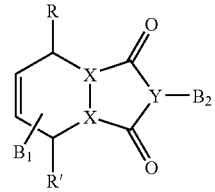

wherein R and R' are independently H or methyl, or together constitute $CH_2$, $CH_2CH_2$, or O; X is CH or N; Y is N, CH═C, or NH—N; and $B_1$ comprises a carbohydrate and $B_2$ comprises a peptide carrier, a protein carrier, or a polysaccharide carrier, or $B_1$ comprises a peptide carrier, a protein carrier, or a polysaccharide carrier and $B_2$ comprises a carbohydrate; and wherein $B_1$ is attached at a ring position that is the same ring position as R or R' and $B_1$ and $B_2$ are each individually optionally attached to the ring structure via a linker.

7. A pharmaceutical composition comprising a conjugate according to claim 1, further comprising a pharmaceutically acceptable carrier.

8. The conjugate of claim 1 wherein the $B_1$ or $B_2$ carbohydrate comprises an oligosaccharide or a polysaccharide.

9. The conjugate of claim 1 wherein the $B_1$ or $B_2$ carbohydrate comprises a hapten or an antigen.

10. The conjugate of claim 1 wherein the $B_1$ or $B_2$ carbohydrate comprises a polysaccharide hapten or antigen.

11. The immobilized biomolecule of claim 6 wherein the $B_1$ or $B_2$ carbohydrate comprises an oligosaccharide or a polysaccharide.

12. The immobilized biomolecule of claim 6 wherein the $B_1$ or $B_2$ carbohydrate comprises a hapten or an antigen.

13. The immobilized biomolecule of claim 6 wherein the $B_1$ or $B_2$ carbohydrate comprises a polysaccharide hapten or antigen.

* * * * *